(12) United States Patent
Ruokokoski et al.

(10) Patent No.: US 11,980,775 B2
(45) Date of Patent: *May 14, 2024

(54) AUTOMATIC GENERATION OF RADIATION TREATMENT PLAN OPTIMIZATION OBJECTIVES

(71) Applicant: Varian Medical Systems International AG, Steinhausen (CH)

(72) Inventors: Emmi Ruokokoski, Helsinki (FI); Jarkko Y. Peltola, Tuusula (FI); Esa Kuusela, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 925 days.

This patent is subject to a terminal disclaimer.

(21) Appl. No.: 17/010,184

(22) Filed: Sep. 2, 2020

(65) Prior Publication Data
US 2020/0398080 A1  Dec. 24, 2020

Related U.S. Application Data

(63) Continuation of application No. 15/706,260, filed on Sep. 15, 2017, now Pat. No. 10,792,514.

(51) Int. Cl.
*A61N 5/10* (2006.01)
*G06F 21/84* (2013.01)
*G06F 30/30* (2020.01)

(52) U.S. Cl.
CPC .......... *A61N 5/1031* (2013.01); *A61N 5/1036* (2013.01); *A61N 5/1038* (2013.01); *A61N 5/1037* (2013.01); *A61N 2005/1041* (2013.01); *G06F 21/84* (2013.01); *G06F 30/30* (2020.01)

(58) Field of Classification Search
CPC .. A61N 5/1031; A61N 5/1036; A61N 5/1038; A61N 5/1037; A61N 2005/1041; G06F 21/84; G06F 30/30
See application file for complete search history.

(56) References Cited

U.S. PATENT DOCUMENTS

| 9,925,391 | B2 | 3/2018 | Carpenter |
| 10,252,081 | B2 | 4/2019 | Kauppinen |
| 10,293,180 | B2 | 5/2019 | Carpenter |

(Continued)

*Primary Examiner* — Courtney D Thomas
(74) *Attorney, Agent, or Firm* — Fitch, Even, Tabin & Flannery LLP

(57) ABSTRACT

Generally speaking, pursuant to these various embodiments a memory stores prescribed treatment instructions for a particular patient radiation therapy. Those treatment instructions specify clinical metrics for goals pertaining to at least one treatment volume for the particular patient. Either directly or inferentially those clinical metrics are prioritized. A control circuit automatically converts those treatment instructions into resultant radiation treatment plan optimization objectives where the automatic conversion can compatibly comprise a non-convex optimization objective. The control circuit then automatically iteratively optimizes the radiation treatment plan for the particular patient radiation therapy as a function, at least in part, of the aforementioned resultant optimization objectives to thereby produce an optimized radiation treatment plan for the particular patient that a radiation treatment platform then utilizes to administer therapeutic radiation to the particular patient.

20 Claims, 5 Drawing Sheets

(56) References Cited

U.S. PATENT DOCUMENTS

| | | |
|---|---|---|
| 10,792,514 B2 * | 10/2020 | Ruokokoski ......... A61N 5/1036 |
| 2013/0085343 A1 | 4/2013 | Toimela |
| 2015/0235143 A1 | 8/2015 | Eder |
| 2015/0317449 A1 | 11/2015 | Eder |
| 2015/0324548 A1 | 11/2015 | Eder |
| 2017/0087382 A1 | 3/2017 | Kauppinen |
| 2018/0052962 A1 | 2/2018 | Van Der Koijk |
| 2018/0236267 A1 | 8/2018 | Kuang |
| 2019/0046813 A1 | 2/2019 | Zhou |

* cited by examiner

AUTOMATIC GENERATION OF RADIATION TREATMENT PLAN OPTIMIZATION OBJECTIVES

CROSS-REFERENCE TO RELATED APPLICATION

This is a continuation of U.S. patent application Ser. No. 15/706,260, filed Sep. 15, 2017, which is hereby incorporated herein by reference in its entirety.

TECHNICAL FIELD

These teachings relate generally to the optimization and use of radiation-therapy treatment plans.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient while using a particular radiation treatment platform. For example, many treatment plans provide for exposing the target volume to possibly varying dosages of radiation from a number of different directions. Arc therapy, for example, comprises one such approach.

Such treatment plans are often optimized prior to use. It will be understood that the expression "optimize," "optimized," and "optimizing" as used herein should not be confused with the idea of identifying an objectively "optimum" plan that is superior to all other possible plans. Instead, such optimization comprises iteratively assessing alternatives to a given plan to typically identify a series of successively-better plans. This can comprise, for example, trying and evaluating iterative alterations to each (or many) of the aforementioned operating parameters Many such treatment plans (such as treatment plans for intensity modulated radiation therapy (IMRT)) are typically based upon so-called objectives, at least some of which are typically derived from a prescribing physician's treatment instructions that specify clinical metrics for goals pertaining at least to the patient's treatment volume and sometimes to adjacent so-called organs-at-risk (OAR) as well. Generally speaking, these optimization objectives are used by the optimizer as the building blocks of a cost function. In particular, a desired dose distribution corresponds to the microscopic state that minimizes these user-defined cost functions.

Developing suitable instructions for a radiation treatment platform that meets the clinical metrics of a prescribed set of treatment instructions is anything but intuitive. While developing a radiation treatment plan via automatically iterated optimization techniques constitutes a well understood prior art endeavor, creating useful optimization objectives from the clinical metrics that comprise a prescribed treatment instruction remains a difficult task that generally requires considerable human input, assistance, and oversight.

More particularly, this human oversight must incorporate and reflect experience and training to achieve better results. It is not unusual for a human technician to modify optimization objectives many times during the optimization process in order to produce a plan and dosing that fulfills the clinical features specified in the treatment instructions. In addition, the conversion of clinical goals into optimization objectives can depend on the geometrical correlations between different goals.

BRIEF DESCRIPTION OF THE DRAWINGS

The above needs are at least partially met through provision of the apparatus and method for automatic generation of radiation treatment plan optimization objectives described in the following detailed description, particularly when studied in conjunction with the drawings, wherein.

Figure 1:
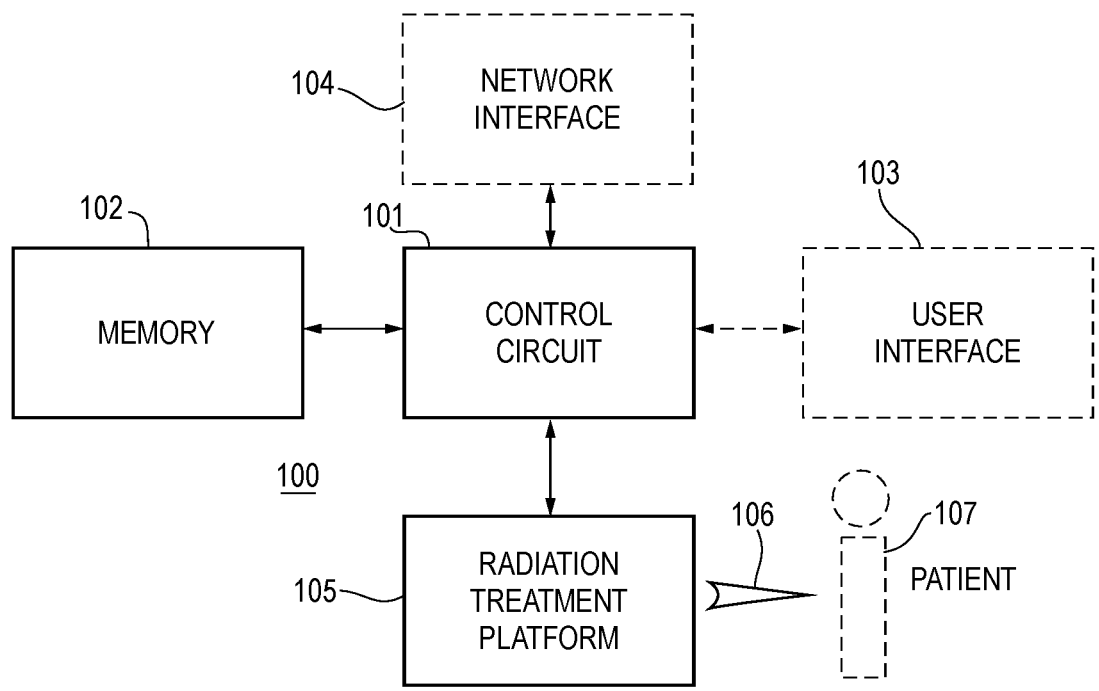
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a memory stores prescribed treatment instructions for a particular patient radiation therapy. Those treatment instructions specify clinical metrics for goals pertaining to at least one treatment volume for the particular patient. Either directly or inferentially those clinical metrics are prioritized. A control circuit automatically converts those treatment instructions into resultant radiation treatment plan optimization objectives where the automatic conversion can compatibly comprise a non-convex optimization objective. The control circuit then automatically iteratively optimizes the radiation treatment plan for the particular patient radiation therapy as a function, at least in part, of the aforementioned resultant optimization objectives to thereby produce an optimized radiation treatment plan for the particular patient that a radiation treatment platform then utilizes to administer therapeutic radiation to the particular patient.

The aforementioned automatic conversion, by one approach, can further compatibly comprise any of a convex optimization objective, a spatial feature-based objective, and/or and an optimization objective that specifies clinical indexes that describe how well a dose cloud conforms to the treatment.

By one approach, if desired, the control circuit can further serve to automatically select one or more supplemental radiation treatment plan optimization objectives that do not directly correspond to any of the aforementioned treatment instructions. The control circuit can then utilize such supplemental radiation treatment plan optimization objectives when iteratively optimizing the radiation treatment plan. Examples include so-called Equivalent Uniform Dose (EUD) objectives for target volumes and/or organs at risk that are considered either parallel or serial.

As another example, the supplemental objective can comprise a knowledge-based objective that comes from a learning model such as Varian Medical System's RapidPlan knowledge-based treatment planning system. These objectives can be generated at the start of the automatic optimization process and can serve to push each organ at risk dose volume histogram to within a range of DVH's that are typically achieved.

By one approach the control circuit simultaneously utilizes all of the aforementioned objectives when automatically iteratively optimizing the radiation treatment plan. By another approach, however, the control circuit can, at least initially, use some, but not all, of the optimization objectives. For example, by one approach the control circuit can first employ objectives that correspond to more highly-prioritized treatment instructions and then subsequently employ objectives that correspond to less highly-prioritized treatment instructions.

If desired, the control circuit can be further configured to employ one or more temporary hard constraints to temporarily hold a plan result corresponding to an important one of the optimization objective while further iteratively optimizing the radiation treatment plan to thereby protect a desired result for that important optimization objective notwithstanding further iterative optimization.

So configured, these teachings provide for forming a radiation treatment plan that can achieve a desired dose distribution without a human needing to manually define optimization objectives beyond the prescribed treatment instructions. In addition, these teachings permit these automatically generated objectives, and the way they are handled by the optimizer, to be dependent at least in part upon a level of priority that can be associated with a given objective.

These and other benefits may become clearer upon making a thorough review and study of the following detailed description. Referring now to the drawings, and in particular to FIG. 1, an illustrative apparatus 100 that is compatible with many of these teachings will now be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as prescribed treatment instructions for a particular patient's radiation therapy and/or supplemental radiation treatment plan optimization objectives as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

By one optional approach the control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

By another optional approach (in lieu of the foregoing or in combination therewith), the control circuit 101 can also operably couple to a network interface 104. So configured the control circuit 101 can communicate with other elements such as information sources and/or processing resources (both within the apparatus 100 and external thereto) via the network interface 104. Network interfaces, including both wireless and non-wireless platforms, are well understood in the art and require no particular elaboration here.

In this illustrative example the control circuit 101 also operably couples to a radiation treatment platform 105 configured to deliver therapeutic radiation 106 to a corresponding patient 107. These teachings are generally applicable for use with any of a wide variety of radiation treatment platforms.

In a typical application setting the radiation treatment platform will include an x-ray source. The x-ray source can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons.

A typical radiation treatment platform 105 may also include one or more support surfaces (such as a couch) to support the patient 107 during the treatment session, a gantry or other mechanism to permit selective movement of the x-ray source, and one or more components (such as jaws, multi-leaf collimators, and so forth) to provide selective beam shaping and/or beam modulation as desired.

As the foregoing elements and systems are well understood in the art, further elaboration in these regards is not provided here except where otherwise relevant to the description.

Figure 2:
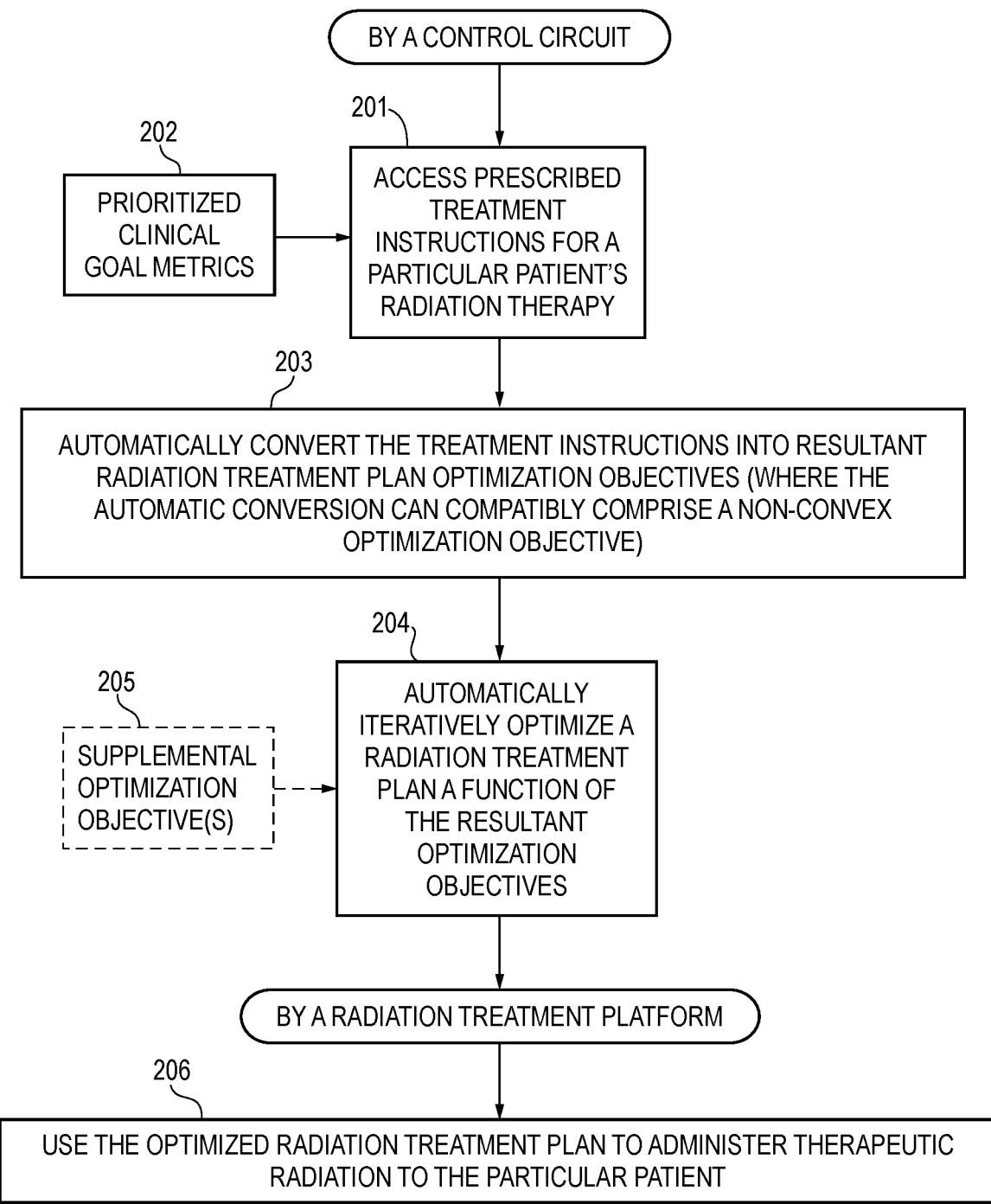
FIG. 2 comprises a flow diagram as configured in accordance with various embodiments of these teachings.

FIG. 2 presents a process 200 that comports with these teachings and that can be carried out with the above-described apparatus 100. The initial activities of this process 200 can be carried out, for example, by the above-described control circuit 101.

At block 201 the control circuit 101 accesses the above-described memory 102 to thereby access prescribed treatment instructions for a particular patient's radiation therapy. As shown in FIG. 2, these prescribed treatment instructions can wholly or at least partially comprise prioritized clinical goal metrics 202. The goals can pertain, for example, to at least one treatment volume (such as a tumor) for the particular patient. These teachings will also accommodate goals that pertain, for example, to so-called organs at risk and/or other structures that may be pertinent to the patient's treatment.

Figure 4:
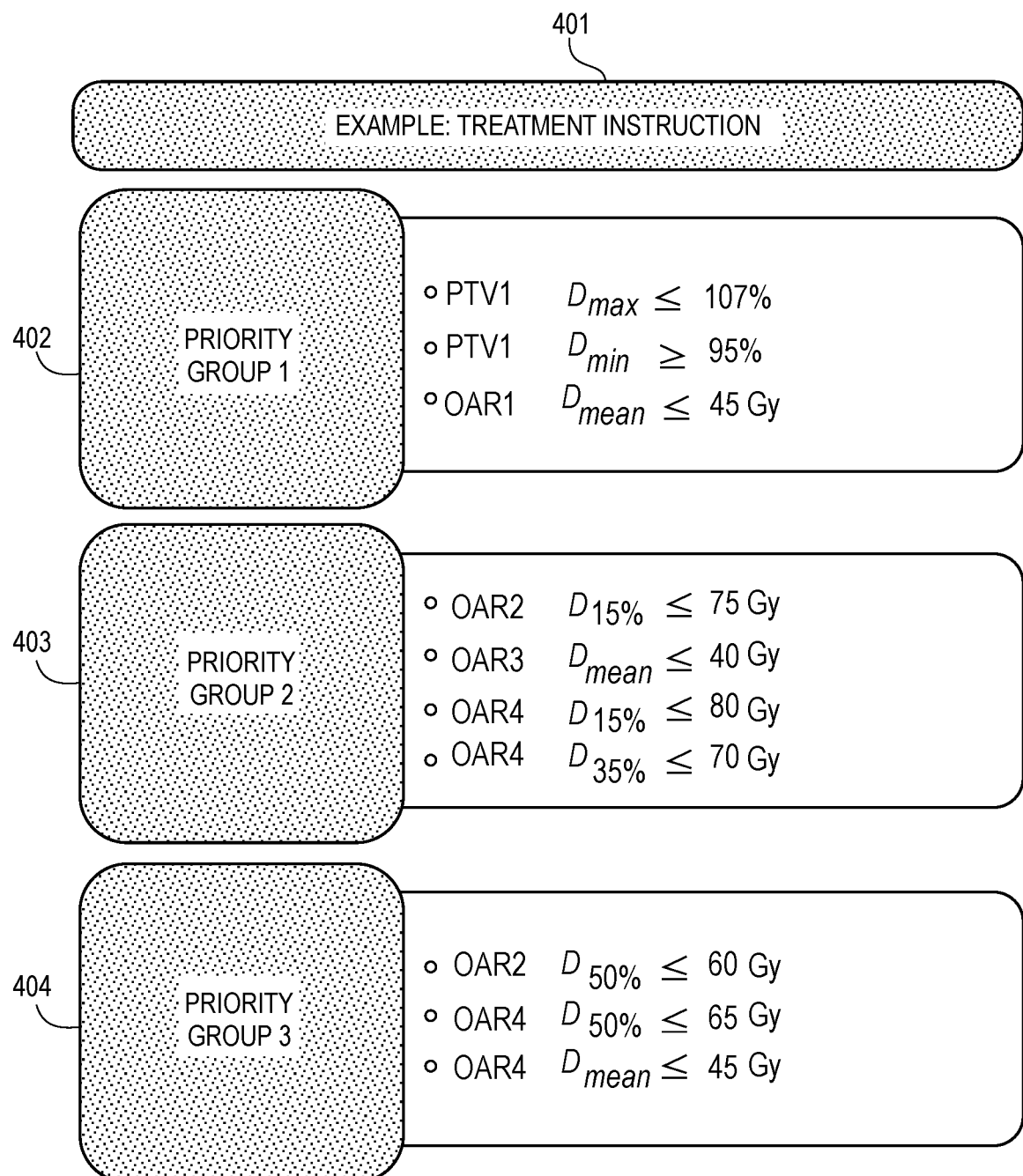
FIG. 4 illustrates treatment instructions per an illustrative example.

FIG. 4 provides an illustrative example of treatment instructions 401. It will be understood that the specifics of this example are intended to serve only in an illustrative capacity and are not intended to suggest any specific limitations with respect to these teachings.

These treatment instructions 401 are typically prescribed by the patient's physician. That said, in a typical application setting the physician may receive input from a variety of other sources including non-physicians. As noted above, these treatment instructions 401 comprise clinical metrics for goals pertaining to volumes corresponding to the particular patient. In this example these goals are explicitly prioritized into three groups. These teachings will also accommodate situations, however, where the goals are not explicitly prioritized but are instead implicitly prioritized (for example, by virtue of a sequenced order of presentation).

In the first priority group 402 the treatment instructions 401 specify explicit clinical metrics for a first patient treatment volume (PTV1), in this case a radiation dose that does not exceed 107 percent and that is at least 95 percent of the target prescription. This first priority group 402 of the treatment instructions 401 further specify that the mean dosage shall not exceed 45 Gy for the first organ at risk (OAR1).

In the second priority group 403 the treatment instructions 401 specify explicit clinical metrics for three other organs at risk (i.e., OAR2, OAR3, and OAR4). And the third priority group 400 specifies additional explicit clinical metrics for two of the already-identified organs at risk (OAR2 and OAR4).

Again, it should be clear that the present teachings are not limited to the specific dosages and dosage specifications presented in FIG. 4. It will also be evident to those skilled in the art that there is nothing particularly unusual or special about this illustrative treatment instruction 401.

Referring again to FIG. 2, at block 203 the control circuit 101 automatically converts the aforementioned treatment instructions into resultant radiation treatment plan optimization objectives. Importantly, this automatic conversion can compatibly yield/comprise a variety of different categorical types of optimization objectives including specifically non-convex optimization objective. (It shall be understood that this reference to "compatibly comprise a variety of different categorical types of optimization objectives" does not mean that any given resultant optimization objective must be any particular type of objective, but rather shall be understood to mean that the process has the intrinsic and inherent ability to create a particular type of objective. This is different from some approaches that, for example, are only capable of forming a convex optimization objective.)

If desired, this automatic conversion can also compatibly yield/comprise a convex optimization objective. In addition, and again if desired, this automatic conversion can further compatibly comprise a spatial feature-based objective and/or optimization objective specifying clinical indexes that described how well a dose cloud conforms to the treatment volume. For example, an objective based upon how the dose is distributed outside the target volume can be useful (to avoid, for example, hot spots (or stripes) of dosage in the body dose cloud). As another example, an objective based upon how the dose is distributed within an organ that is near (or even overlapping with) the target volume can be useful.

These teachings will accommodate, when appropriate, deriving only a single resultant radiation treatment plan optimization objective. In many application settings, however, it may be useful to derive multiple optimization objectives. By one approach there may be one or more optimization objectives for each expressed clinical metric in the treatment instructions. By another approach a single optimization objective may be derived as a function of two or more of the clinical metrics contained in the treatment instructions.

By one useful approach the created optimization objectives are tighter than the actual treatment goals. For example, the treatment instructions may prescribe a particular dose X Gy for a particular treatment volume and may also specify that the dose cannot exceed 107 percent of X Gy nor can the dose be less than 95 percent of X Gy. The automatically generated objectives for that treatment target, however, could specify a lower dose-volume objective at (dose, volume)-point (98% dose, 100% volume) and an upper dose-volume objective at (dose, volume)-point (105% dose, 0% vol).

Using such an approach the organ at risk objectives that correspond to the goal may typically be a few percentages tighter than the treatment instruction goal in both the volume and the dose axis. For example, for an organ at risk treatment instruction goal of $D_{15\%} \leq 75$ Gy the control circuit 101 could automatically create an upper objective such as (0.98*75 Gy, 0.98*15% volume).

It will be understood that these values are only initial values and during the iterations of the optimization process the process will tighten or loosen the values as needed to achieve the higher goals and to tighten loose goals. It will also be understood that the weights applied to the created objectives will depend on the goals' relative order and their respective priority.

At block 204 the control circuit 101 then automatically iteratively optimizes the radiation treatment plan for the particular patient's radiation therapy as a function, at least in part, of the resultant optimization objectives to produce an optimized radiation treatment plan for the particular patient. By one approach, this automatic iterative optimization can comprise any of a variety of already-known approaches in these regards. In that case, the automatically derived optimization objectives are simply utilized as the governing objectives for the automatic iterative optimization process of choice.

As suggested by optional block 205, this process 200 will also accommodate providing and using one or more supplemental radiation treatment plan optimization objectives. Being "supplemental," these optimization objectives are not part of the aforementioned automatically derived resultant radiation treatment plan optimization objectives and do not (necessarily) directly correspond to any of the treatment instructions per se. These supplemental optimization objectives, however, may nevertheless be suitable for use in order to accommodate information regarding the particular radiation treatment platform for which the radiation treatment plan is being optimized and/or to accommodate other clinical or historical information that may be suitably leveraged in favor of a good outcome for the patient.

By one approach, these teachings will accommodate supplemental optimization objectives that are expressed, at least in part, as a dose volume histogram (DVH). An example of an automatically created DVH optimization objective could be a preferred target DVH that gives more information regarding the target DVH as compared to providing, for example, only minimum and maximum DVH-points.

Generally speaking DVH's typically represent three-dimensional dose distributions in a graphical two-dimensional format (the three-dimensional dose distributions being created, for example, in a computerized radiation-treatment planning system based on a three-dimensional reconstruction of an X-ray computed tomography scan and study). The "volume" referred to in DVH analysis can be, for example, the radiation-treatment target, a healthy organ located near such a target, an arbitrary structure, and so forth.

DVH's are often visualized in either of two ways: as differential DVH's or as cumulative DVH's. With differential DVH's column height for a given dose bin corresponds to the volume of the structure that receives that dose. Bin doses typically extend along the horizontal axis while structure volumes (either percent or absolute volumes) extend along the vertical axis.

A cumulative DVH is typically plotted with bin doses along the horizontal axis but has a column height for the first bin that represents the volume of structure(s) that receive greater than or equal to that dose. The column height of the second bin then represents the volume of structure(s) that receive greater than or equal to that dose, and so forth. With high granularity a cumulative DVH often appears as a smooth line graph. For many application settings cumulative DVH's are preferred over differential DVH's but these teachings can accommodate either approach.

Figure 3:
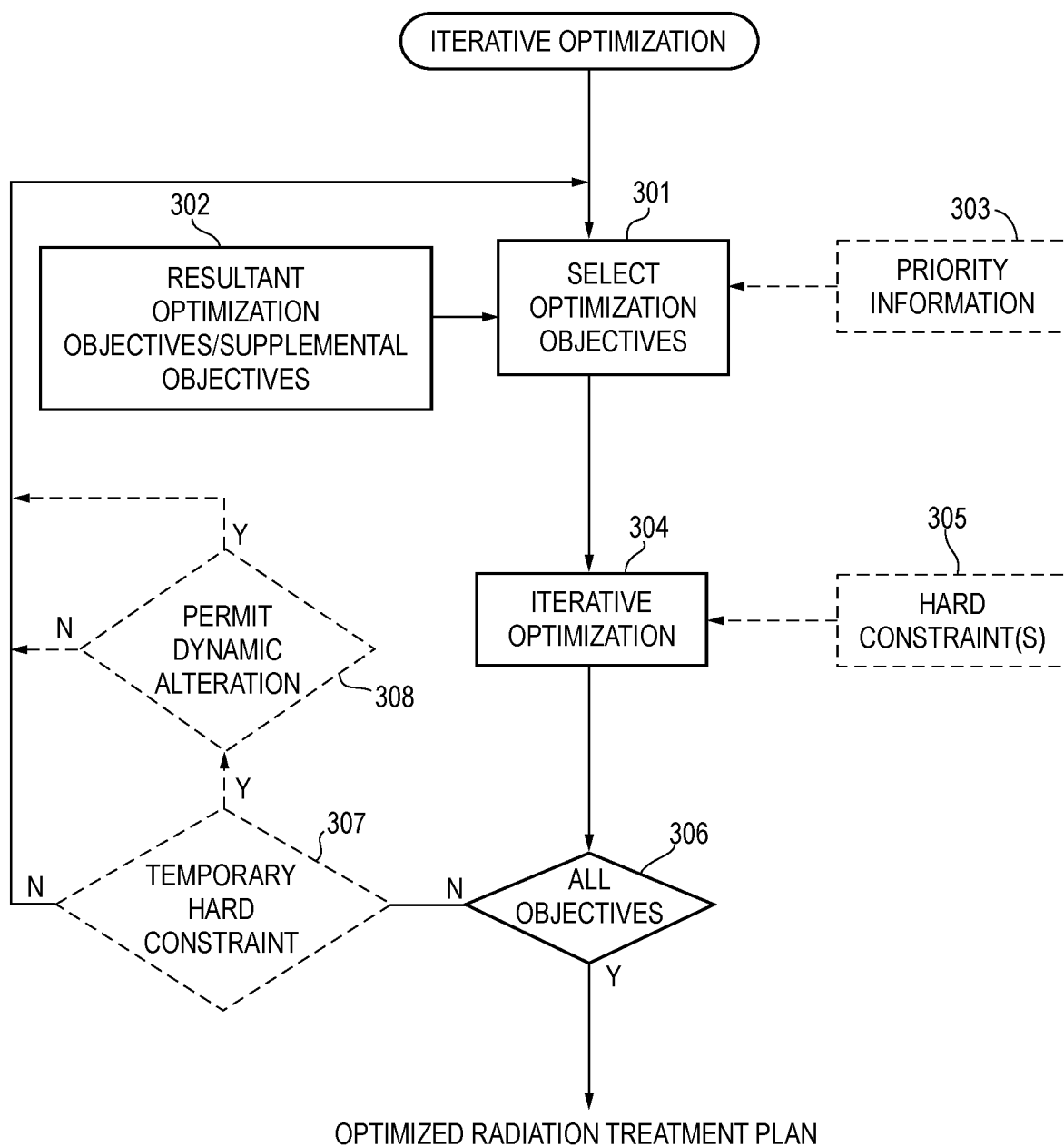
FIG. 3 comprises a flow diagram as configured in accordance with various embodiments of these teachings.

FIG. 3 presents more specific examples regarding the iterative optimization process 204. In this example, at block 301 the control circuit 101 selects optimization objectives to utilize when iteratively optimizing the radiation treatment plan. As noted above, by one approach this can comprise selecting all of the available objectives and then utilizing them simultaneously while iteratively optimizing the radiation treatment plan.

By another approach, however, the control circuit 101 may initially select fewer than all of the available optimization objectives 302 (including fewer than all of the available resultant radiation treatment plan optimization objectives that were automatically converted from the treatment instructions). As noted above, the original treatment instructions may include explicit or implicit prioritization information 303 regarding the clinical metrics for goals that comprise the treatment instructions. In this case, the control circuit 101 may select to initially use a subset comprising one or more of the automatically derived optimization objectives that correlate to the most highly-prioritized treatment instructions.

At block 304 the control circuit 101 then utilizes the iterative optimization methodology of choice in view of the selected optimization objective(s). Upon concluding this activity, the control circuit 101 then determines, at decision block 306, whether all of the optimization objectives have been applied. When true, the control circuit 101 can output the corresponding optimized radiation treatment plan.

When not true, however, the control circuit 101 circles back to reoptimize the radiation treatment plan using one or more additional optimization objectives. This can comprise, at block 301, selecting previously unselected automatically derived optimization objectives that correspond to less highly-prioritized treatment instructions. This can also comprise, if desired, using one or more of the aforementioned supplemental radiation treatment plan optimization objectives that do not directly correspond to any of the treatment instructions.

By one approach, certain previously-achieved results using a previous (perhaps more highly-prioritized optimization objective) are allowed to change as new optimization objectives are added and considered. While such an approach can sometimes be useful, there can also be situations where such changes are antithetical to achieving a "best" result. For example, the tumor to be purposefully irradiated may be very near to an especially at-risk organ. The treatment instructions may therefore prescribe protecting that at-risk organ with high priority. In such a case, allowing the treatment plan to worsen the protection that has been already-achieved achieved for that organ during earlier optimization iterations may be undesirable.

To accommodate such concerns, and as shown at optional block 307, these teachings will accommodate having the control circuit 101 decide whether to employ one or more temporary hard constraints to temporarily hold a currently-achieved radiation treatment plan result that corresponds, for example, to a particular patient volume. In particular, the constrained result can correspond to an important one (i.e., a highly prioritized one) of the resultant optimization objectives.

More specifically, pursuant to this process the control circuit 101 decide whether to employ a temporary hard constraint before conducting further iterations of the optimization process using a newly-introduced resultant optimization objective. (This same approach can be utilized before introducing a supplemental objective, if desired.) So configured, this approach can protect a desired result for an important one (or more) of the resultant optimization objectives notwithstanding further iterative optimization.

As already noted, this hard constraint that prevents changes with respect to a particular currently-achieved radiation treatment plan result (such as, for example, a particular level of dosing for a particular treatment volume or organ at risk) can be only temporarily applied. The duration can be optionally set by the control circuit 101 if desired. By one approach the duration is time-based and will be maintained, for example, for a particular number of seconds or minutes of processing activity. By another approach the duration is milestone based and might be maintained, for example, for a specific number of iterations or until a particular result is achieved during the iterative optimization process. By yet another approach the hard constraint may be temporarily applied until the control circuit 101 specifically releases application of the constraint per some other criterion.

These teachings will permit other approaches in these regards. For example, and as illustrated at block 308, by one approach the control circuit 101 can decide whether to nevertheless permit dynamic alteration of a temporarily-applied hard constraint during the iterative optimization process upon introducing a new optimization objective per the foregoing. Such dynamic alterations can comprise, for example, changes with respect to location, weighting, and/or type. Again, this dynamically permitted alteration may be subject to constraints regarding when an alteration is permitted and/or a magnitude of the alteration that is permitted.

By one approach, if desired, once all objectives have been processed via the iterative optimization process the control circuit 101 can check to determine whether any goals have in fact not been met. Upon identifying an unmet goal, the control circuit 101 can be configured to reengage the iterative optimization process to further try to achieve those goals while not undoing or lessening already-achieved higher priority results. The unmet goals may not be goals that are specifically articulated in the original treatment instructions. For example, the unmet goal may be a goal to minimize organ at risk doses (measured, for example, as a mean) as much as possible. As another example, the unmet goal may be to minimize the needed Monitor Unit (MU) count as much as possible (Monitor Units being a known metric in this art). Such features are generally viewed as being universally good and may typically be worth pursuing so long as already achieved desired results are not undone.

Figure 5:
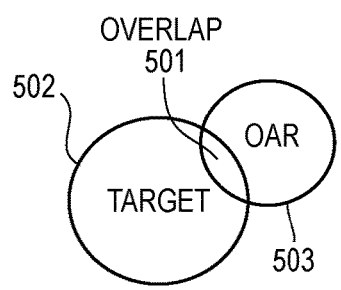
FIG. 5 comprises a schematic representation.

By one approach, the control circuit 101 may be configured to automatically handle target and organ at risk overlaps. FIG. 5 presents a simple illustrative example of an overlap 501 between a target volume 502 and an organ at risk 503.

Figure 6:
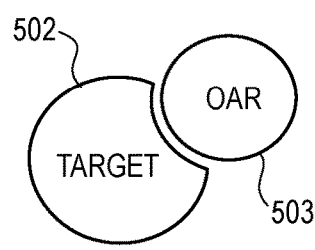
FIG. 6 comprises a schematic representation.

As a first example, and referring to FIG. 6, an organ at risk 503 overlaps (from the point of view of the source of radiation) with a target structure 502 and the goal associated with the organ at risk 503 is of higher priority than the target goal. In this case the control circuit 101 can automatically create a so-called Planning Organ-at-risk Volume (PRV) structure from the organ at risk by adding a small margin to the organ at risk as shown. Using this approach the target objective is only applied to the part of the target 502 that is left when the PRV has been cropped out from the target 502.

Figure 7:
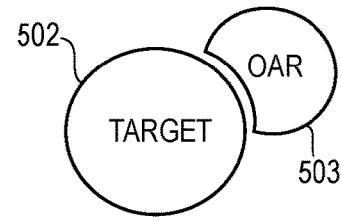
FIG. 7 comprises a schematic representation.

As another example, and referring to FIG. 7, assuming the same overlapping situation described above but now the target goal has a higher priority as compared to the organ at risk priority. In this case the control circuit 101 can add a small margin to the target structure and apply the organ at risk objective only to the part of the organ at risk from which the target margin has been cropped out. Such margins can help to ensure steep dose fall-off.

Referring again to FIG. 2, upon achieving a satisfactory optimized radiation treatment plan, the aforementioned radiation treatment platform 105 can use, at block 206, that plan to administer therapeutic radiation to the particular patient 107.

So configured, these teachings provide for automatically converting clinical goals into optimization objectives and for then adding the optimization objectives one by one (or in small subgroups) in a prioritized manner to the iterative optimization process. These teachings also provide for using temporary hard constraints to hold important goals in achieved optimal positions while processing less important ones.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. As one example in these regards, these teachings can also accommodate automatic simultaneous integrated boost targets.

What is claimed is:

1. An apparatus comprising:
   a memory having stored therein prescribed treatment instructions for a particular patient's radiation therapy, the treatment instructions specifying prioritized clinical metrics for goals pertaining to at least one treatment volume for the particular patient;
   a control circuit operably coupled to the memory and configured to:
      automatically convert the treatment instructions into resultant radiation treatment plan optimization objectives, wherein the automatic conversion can compatibly comprise a non-convex optimization objective; and
      automatically iteratively optimize a radiation treatment plan for the particular patient's radiation therapy as a function, at least in part, of the resultant optimization objectives to produce an optimized radiation treatment plan for the particular patient.

2. The apparatus of claim 1 wherein the automatic conversion can further compatibly comprise any of a convex optimization objective, a spatial feature-based objective, and an optimization objective specifying clinical indexes that describe how well a dose cloud conforms to the treatment volume.

3. The apparatus of claim 1 wherein the control circuit is configured to automatically iteratively optimize the radiation treatment plan for the particular patient's radiation therapy as a function, at least in part, of the optimization objectives by initially using some, but not all, of the resultant optimization objectives.

4. The apparatus of claim 3 wherein the control circuit is configured to initially use some, but not all, of the optimization objectives by first using at least one of the optimization objectives that corresponds to a most highly-prioritized one of the treatment instructions.

5. The apparatus of claim 4 wherein the control circuit is configured to automatically iteratively optimize the radiation treatment plan for the particular patient's radiation therapy as a function, at least in part, of the optimization objectives by, subsequent to using the at least one of the optimization objectives that corresponds to the most highly-prioritized one of the treatment instructions, subsequently using at least one of the optimization objectives that corresponds to a less highly-prioritized one of the treatment instructions.

6. The apparatus of claim 1 wherein the control circuit is further configured to:
automatically select at least one supplemental radiation treatment plan optimization objective that does not directly correspond to any of the treatment instructions; and wherein the control circuit is configured to automatically iteratively optimize the radiation treatment plan for the particular patient's radiation therapy as a function, at least in part, of the resultant optimization objectives and the at least one supplemental radiation treatment plan optimization objective to produce an optimized radiation treatment plan for the particular patient.

7. The apparatus of claim 6 wherein the at least one supplemental radiation treatment plan optimization objective that does not directly correspond to any of the treatment instructions comprises an Equivalent Uniform Dose objective for at least one of a target volume and an organ at risk.

8. The apparatus of claim 6 wherein the at least one supplemental radiation treatment plan optimization objective that does not directly correspond to any of the treatment instructions comprises a knowledge-based objective.

9. The apparatus of claim 1 wherein the control circuit is configured to automatically iteratively optimize a radiation treatment plan for the particular patient's radiation therapy as a function, at least in part, of the resultant optimization objectives to produce an optimized radiation treatment plan for the particular patient by, at least in part, employing at least one temporary hard constraint to temporarily hold a plan result corresponding to an important one of the resultant optimization objectives while further iteratively optimizing the radiation treatment plan in view of at least one newly-added resultant optimization objective to thereby protect a desired result for the important one of the resultant optimization objectives notwithstanding the further iterative optimization.

10. The apparatus of claim 9 wherein the control circuit is further configured to alter the temporary hard constraint while newly adding additional resultant optimization objectives.

11. A method comprising:
by a control circuit:
accessing a memory having stored therein prescribed treatment instructions for a particular patient's radiation therapy, the treatment instructions specifying prioritized clinical metrics for goals pertaining to at least one treatment volume for the particular patient;
automatically converting the treatment instructions into resultant radiation treatment plan optimization objectives, wherein the automatic conversion can compatibly comprise a non-convex optimization objective;
automatically iteratively optimizing a radiation treatment plan for the particular patient's radiation therapy as a function, at least in part, of the resultant optimization objectives to produce an optimized radiation treatment plan for the particular patient.

12. The method of claim 11 wherein automatically converting the treatment instructions into resultant radiation treatment plan optimization objectives can further compatibly comprise any of a convex optimization objective, a spatial feature-based objective, and an optimization objective specifying clinical indexes that describe how well a dose cloud conforms to the treatment volume.

13. The method of claim 11 wherein automatically iteratively optimizing the radiation treatment plan for the particular patient's radiation therapy comprises automatically iteratively optimizing the radiation treatment plan as a function, at least in part, of the optimization objectives by initially using some, but not all, of the resultant optimization objectives.

14. The method of claim 13 wherein initially using some, but not all, of the resultant optimization objectives comprises first using at least one of the optimization objectives that corresponds to a most highly-prioritized one of the treatment instructions.

15. The method of claim 14 wherein automatically iteratively optimize the radiation treatment plan for the particular patient's radiation therapy as a function, at least in part, of the optimization objectives comprises, subsequent to using the at least one of the optimization objectives that corresponds to the most highly-prioritized one of the treatment instructions, using at least one of the optimization objectives that corresponds to a less highly-prioritized one of the treatment instructions.

16. The method of claim 11 further comprising:
automatically selecting at least one supplemental radiation treatment plan optimization objective that does not directly correspond to any of the treatment instructions;
and wherein automatically iteratively optimizing the radiation treatment plan for the particular patient's radiation therapy comprises automatically iteratively optimizing the radiation treatment plan as a function, at least in part, of the resultant optimization objectives and the at least one supplemental radiation treatment plan optimization objective to produce an optimized radiation treatment plan for the particular patient.

17. The method of claim 11 wherein automatically iteratively optimizing a radiation treatment plan for the particular patient's radiation therapy as a function, at least in part, of the resultant optimization objectives to produce an optimized radiation treatment plan for the particular patient further comprises, at least in part, employing at least one temporary hard constraint to temporarily hold a plan result corresponding to an important one of the resultant optimization objectives while further iteratively optimizing the radiation treatment plan in view of at least one newly-added resultant optimization objective to thereby protect a desired result for the important one of the resultant optimization objectives notwithstanding the further iterative optimization.

18. The method of claim 17 further comprising altering the temporary hard constraint while newly adding additional resultant optimization objectives.

19. The method of claim 11 further comprising automatically handling target and organ-at-risk overlaps.

20. The method of claim 11 further comprising:
by a radiation treatment platform:
using the optimized radiation treatment plan to administer therapeutic radiation to the particular patient.

* * * * *